(12) United States Patent
Kang et al.

(10) Patent No.: US 7,993,259 B2
(45) Date of Patent: Aug. 9, 2011

(54) PERCUTANEOUS INTRA-AORTIC VENTRICULAR ASSIST DEVICE

(76) Inventors: Wei-Chang Kang, Tainan (TW); Yu-Li Kang, Tainan (TW)

( * ) Notice: Subject to any disclaimer, the term of this patent is extended or adjusted under 35 U.S.C. 154(b) by 275 days.

(21) Appl. No.: 12/358,681

(22) Filed: Jan. 23, 2009

(65) Prior Publication Data

US 2010/0191035 A1      Jul. 29, 2010

(51) Int. Cl.
*A61N 1/362*      (2006.01)
(52) U.S. Cl. .............................. 600/16; 623/3.1; 600/17
(58) Field of Classification Search .............. 600/16–18; 623/3.1, 3.2, 3.3
See application file for complete search history.

(56) References Cited

U.S. PATENT DOCUMENTS

| | | | | |
|---|---|---|---|---|
| 7,144,364 B2 * | 12/2006 | Barbut et al. | .................. | 600/16 |
| 7,479,102 B2 * | 1/2009 | Jarvik | .............................. | 600/16 |
| 7,544,160 B2 * | 6/2009 | Gross | .............................. | 600/16 |

* cited by examiner

*Primary Examiner* — Niketa I Patel
*Assistant Examiner* — Catherine Voorhees
(74) *Attorney, Agent, or Firm* — Potter Anderson & Corroon LLP (57) ABSTRACT

A percutaneous intra-aortic ventricular assist device is adapted for implantation in an aorta that has a luminal wall, and includes a tubular stent body, an inner tubular body, a vane member, a carrier member, a rib unit, a first pulled string, a second pulled string, an alternately pulling mechanism, and a synchronizing member.

7 Claims, 9 Drawing Sheets

PERCUTANEOUS INTRA-AORTIC VENTRICULAR ASSIST DEVICE

BACKGROUND OF THE INVENTION

1. Field of the Invention

This invention relates to a ventricular assist device, more particularly to a percutaneous intra-aortic ventricular assist device.

2. Description of the Related Art

Heart failure is regarded as one of serious heart diseases and signifies that a heart is unable to pump sufficient amount of blood to other organs and tissues of a human body. High mortality in patients with heart failure arises from a heart that is gradually losing pumping function thereof. A weak left ventricle that is incapable of pumping sufficient blood full of oxygen to other organs and tissues of a human body results in left-sided heart failure that is commonly observed among cases of heart failure.

Generally, four categories of conventional devices for curing left-sided heart failure are available in the market: an intra-aortic balloon pump (IABP), an extracorporeal membrane oxygenator (ECMO), a total artificial heart, and a left ventricular assist device (LVAD). The aforesaid conventional devices are able to assist the weak left ventricle in order to pump sufficient blood. However, the total artificial heart and the LVAD are implanted in a human body by virtue of a complex surgery such as a thoracic surgery. Consequently, the total artificial heart and the LVAD are only suitable for patients with severe left-sided heart failure.

The IABP and the ECMO can be implanted in a human body without performing a thoracic surgery. Nevertheless, the ECMO is not appropriate for long-term use. Even though the IABP can be percutaneously delivered to an aorta, during severe left-sided heart failure, the IABP is unable to successfully assist a left ventricle due to low pump efficiency of the IABP.

A new device that is capable of efficiently assisting a left ventricle, that can be delivered to an aorta through a minimally invasive method, and that is suitable for long-term use is strongly desired.

SUMMARY OF THE INVENTION

Therefore, the object of the present invention is to provide a percutaneous intra-aortic ventricular assist device that can overcome the aforesaid drawbacks of the prior art.

According to this invention, a percutaneous intra-aortic ventricular assist device is adapted for implantation in an aorta that has a luminal wall, and includes a tubular stent body, an inner tubular body, a vane member, a carrier member, a rib unit, a first pulled string, a second pulled string, an alternately pulling mechanism, and a synchronizing member.

The tubular stent body is made from a material expandable at a site of implantation, is configured to be adapted to anchor on the luminal wall of the aorta downstream of an aorta root in terms of an ejected flow of blood under systole pressure, and has an abluminal surface which confronts the luminal wall, and a luminal surface which is opposite to the abluminal surface, and which defines an interior space extending along a central axis in a lengthwise direction.

The inner tubular body is connected to the tubular stent body and has an outer tubular surface which extends along the central axis to define, in cooperation with the luminal surface of the tubular stent body, a surrounding passage, and an inner tubular surface which is opposite to the outer tubular surface in radial directions, which defines an accommodation chamber, and which has a guiding slot unit that extends in the lengthwise direction to terminate at proximal and distal loci relative to the aorta root, and that extends radially through the outer tubular surface to communicate the surrounding passage with the accommodation chamber.

The vane member is disposed to be movable in the surrounding passage between proximal and distal limits that respectively correspond to the proximal and distal loci of the guiding slot unit, and that are apart from each other by a predetermined traveling length, and is configured to help force the ejected flow of the blood downstream when the vane member is moved from the proximal limit towards the distal limit.

The carrier member is disposed to be movable in the accommodation chamber between the proximal and distal loci of the guiding slot unit.

The rib unit is disposed to move along the guiding slot unit, and is configured to interconnect the carrier member and the vane member so as to permit the vane member to be moved with the carrier member.

The first pulled string has first inner and outer ends which are opposite to each other lengthwise, and which are respectively connected to the carrier member and led out of a patient's body such that when the first outer end is pulled externally, the carrier member is moved towards the distal locus of the guiding slot unit.

The second pulled string has second inner and outer ends which are opposite to each other lengthwise, and which are respectively connected to the carrier member and led out of the patient's body such that when the second outer end is pulled externally, the carrier member is moved towards the proximal locus of the guiding slot unit.

The alternately pulling mechanism is disposed to couple with the first and second outer ends respectively such that when the alternately pulling mechanism is actuated to alternately pull the first and second outer ends in a pulling direction respectively to displace the carrier member to the distal and proximal loci of the guiding slot unit respectively, the second and first pulled strings are enabled respectively by alternately pulling of the first and second outer ends to respectively permit the second and first outer ends to tensely retrieve, concomitant with the alternate pulling of the first and second outer ends respectively, the predetermined traveling length in a releasing direction that is opposite to the pulling direction.

The synchronizing member is disposed to couple with the alternately pulling mechanism so as to bring the pulling of the first and second outer ends in the pulling direction in synchronization with the alternate systole and diastole actions.

BRIEF DESCRIPTION OF THE DRAWINGS

Other features and advantages of the present invention will become apparent in the following detailed description of the preferred embodiment of this invention, with reference to the accompanying drawings, in which.

DETAILED DESCRIPTION OF THE PREFERRED EMBODIMENT

Figure 7:
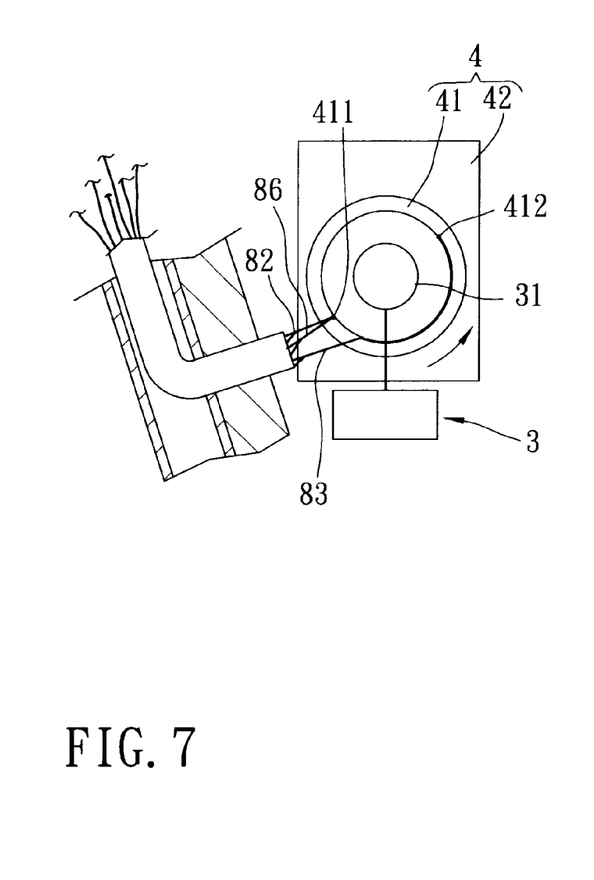
FIG. 7 is a schematic view illustrating how a vane member of the preferred embodiment is transformed to a folded position in an ascending aorta during diastole.
Figure 8:
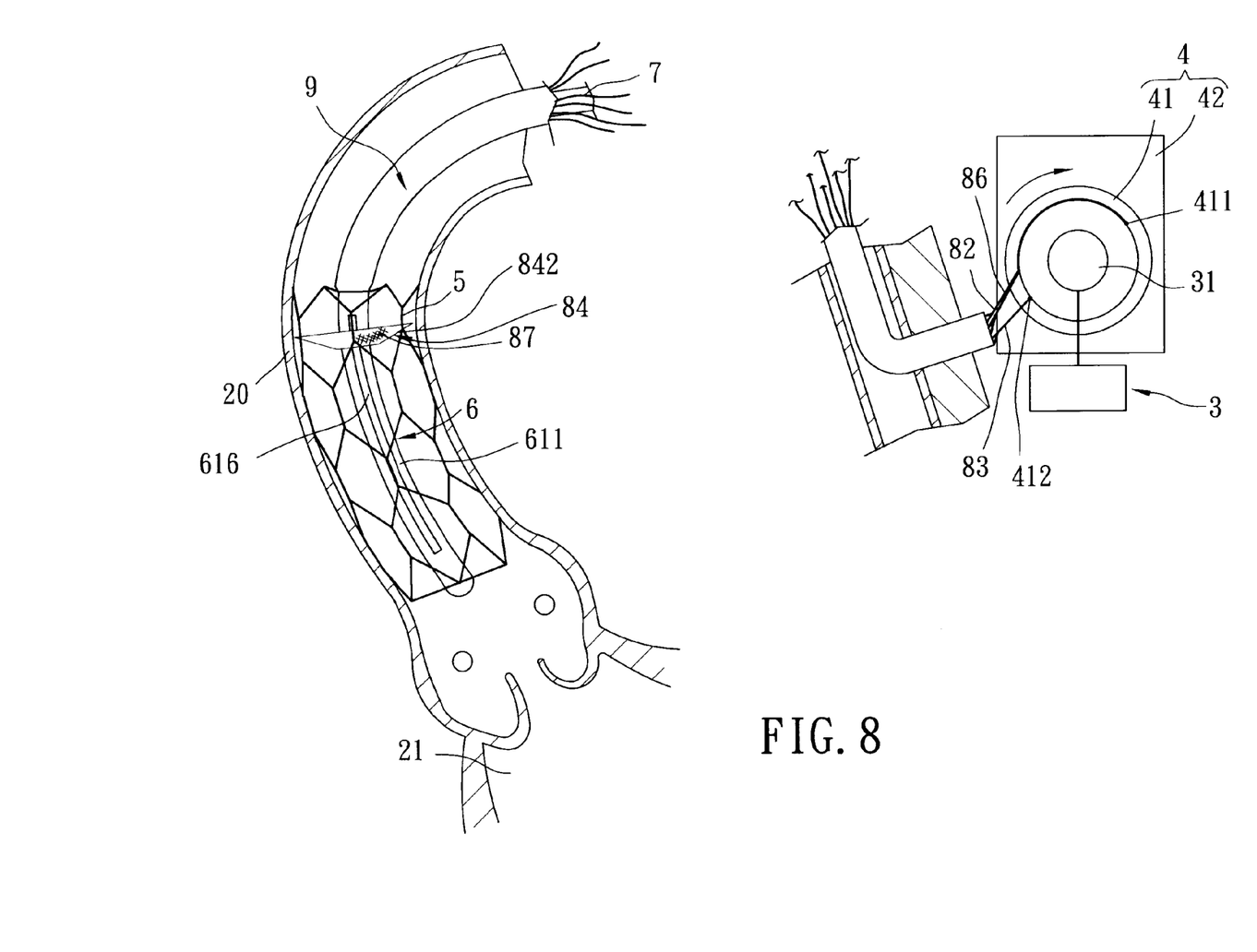
FIG. 8 is a schematic view illustrating how the vane member of the preferred embodiment is transformed to a spread position in the ascending aorta during systole.

Referring to FIGS. 7 and 8, the preferred embodiment of a percutaneous intra-aortic ventricular assist device according to the present invention is adapted for implantation in an aorta that has a luminal wall and is able to assist a left ventricle 21 in pumping blood into an ascending aorta 20.

Figure 1:
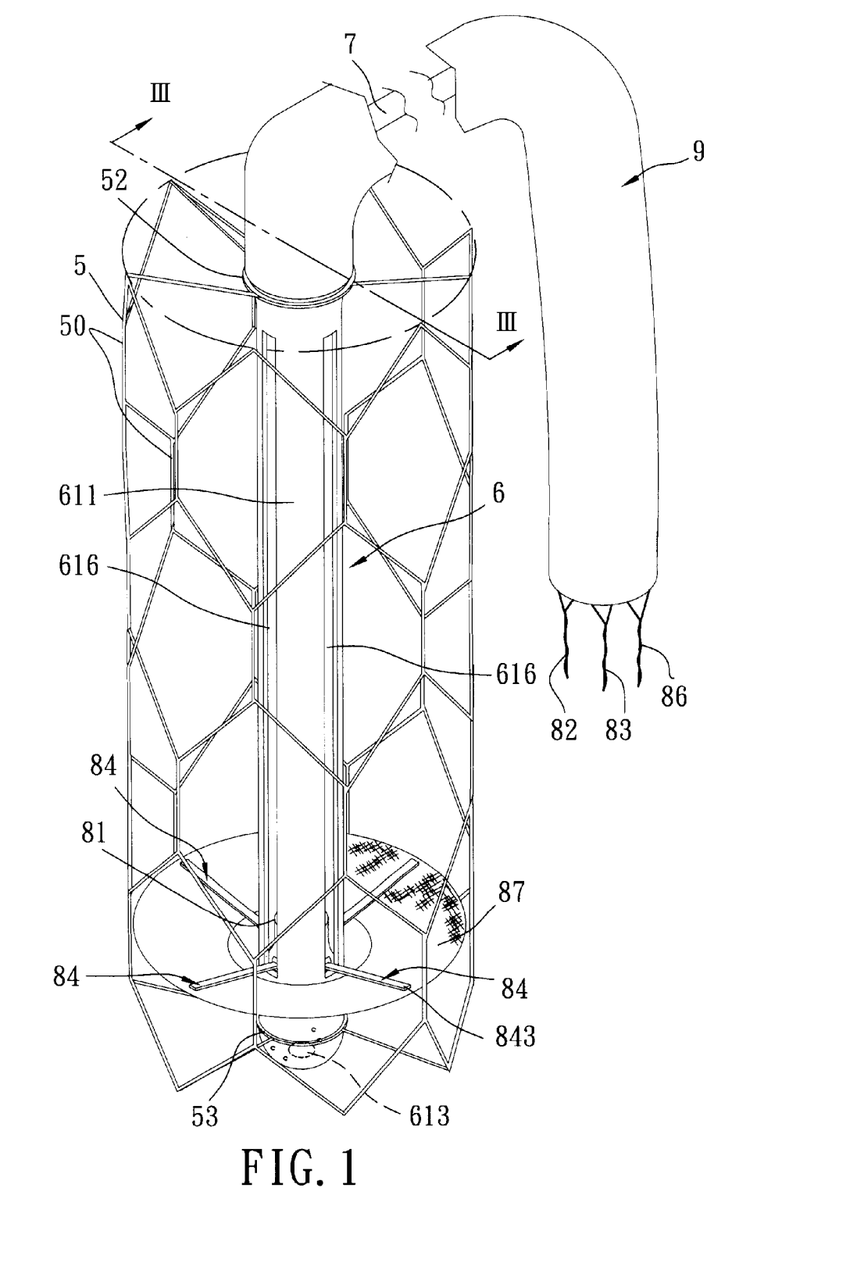
FIG. 1 is a perspective view of the preferred embodiment of a percutaneous intra-aortic ventricular assist device according to this invention.
Figure 2:
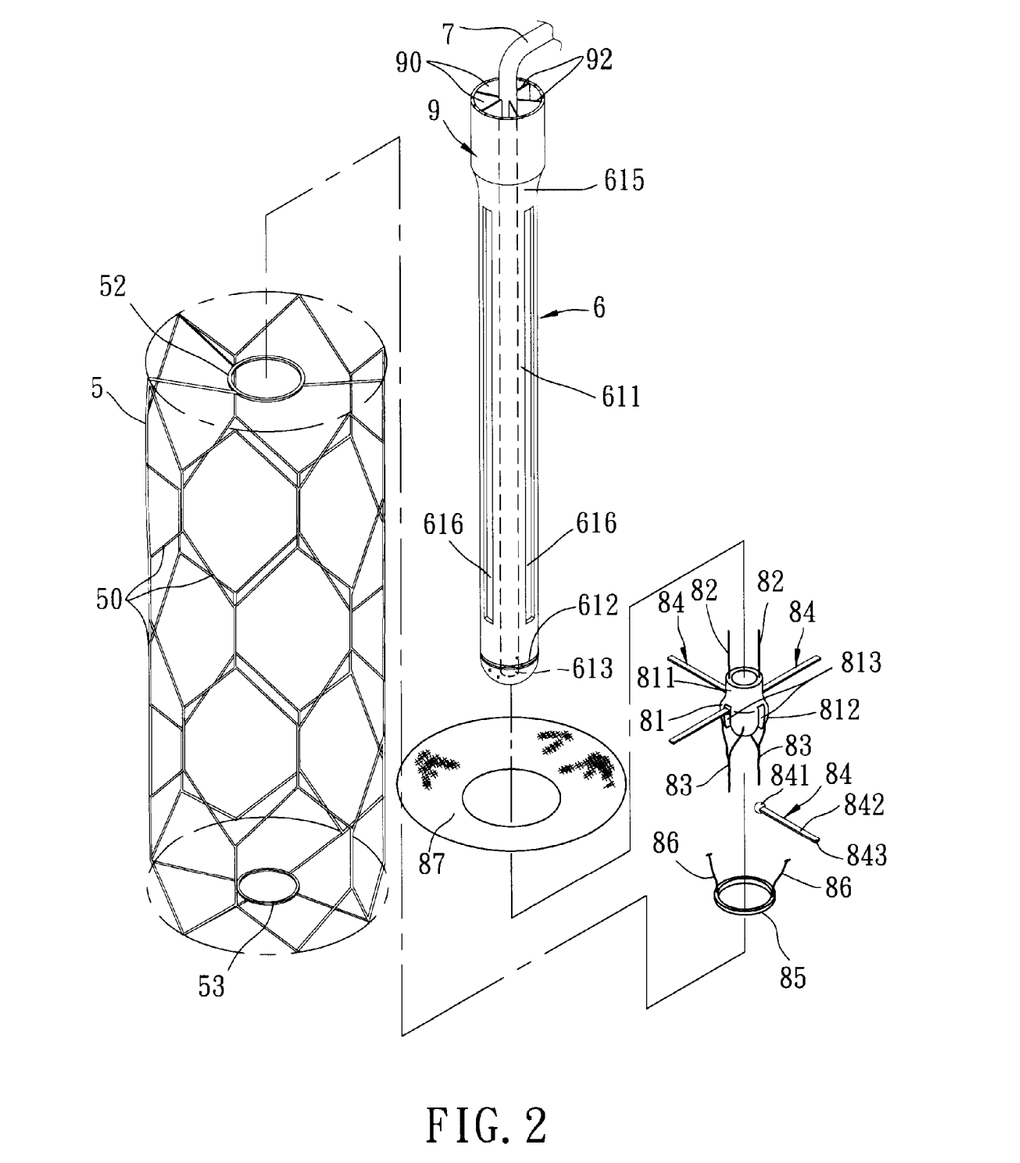
FIG. 2 is a fragmentary partly exploded view of the preferred embodiment shown in FIG. 1.
Figure 3:
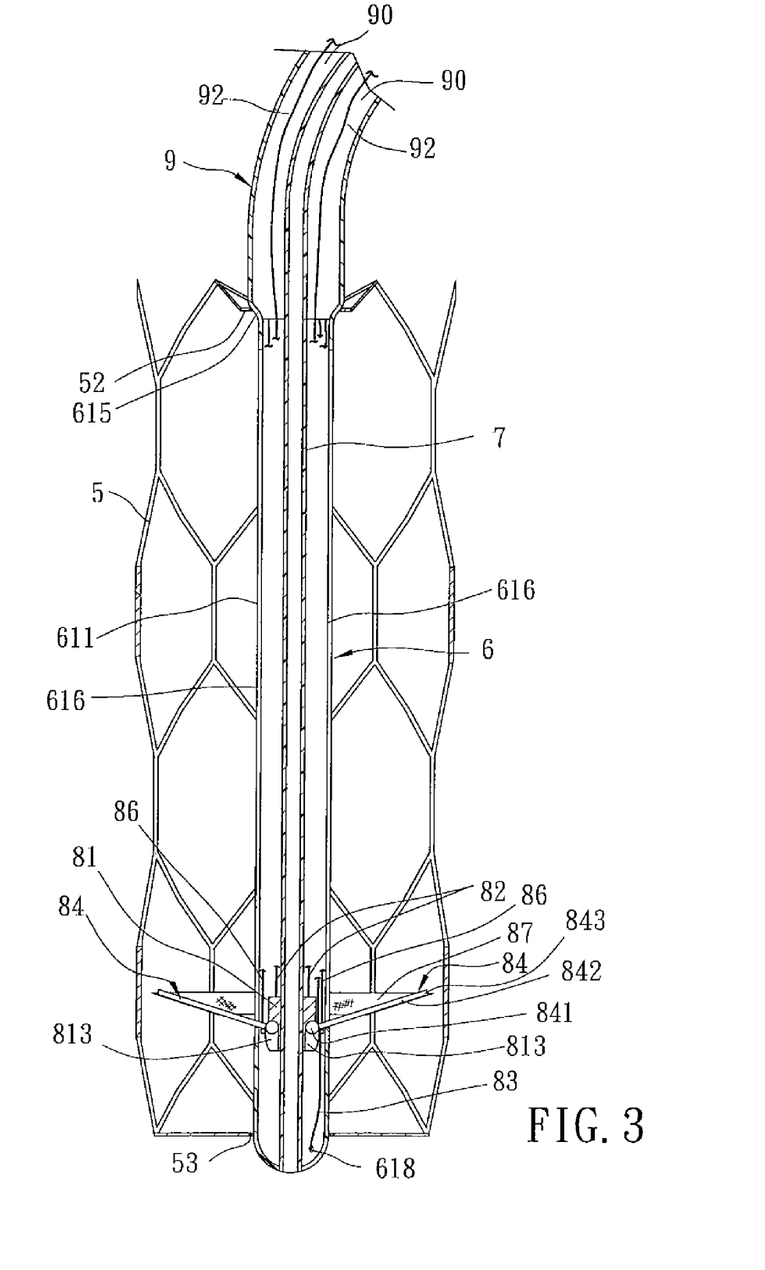
FIG. 3 is a fragmentary sectional view of the preferred embodiment taken along line III-III in FIG. 1.
Figure 4:
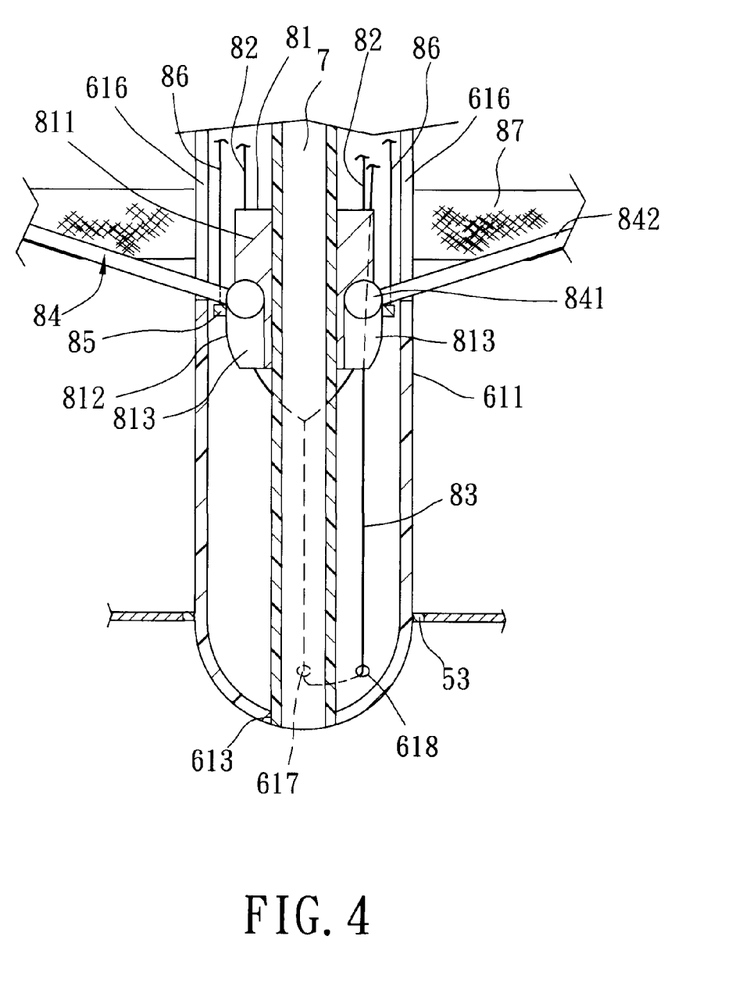
FIG. 4 is a fragmentary magnified view of FIG. 3.

Referring to FIGS. 1, 2, and 3, the percutaneous intra-aortic ventricular assist device includes a tubular stent body 5, an inner tubular body 6, a vane member 87, a carrier member 81, a rib unit, two first pulled strings 82, two second pulled strings 83, an alternately pulling mechanism 4 (shown in FIGS. 7 and 8), and a synchronizing member 3 (shown in FIGS. 7 and 8).

The tubular stent body 5 is made from a material expandable at a site of implantation. In this embodiment, the tubular stent body 5 is made from a plurality of metal struts 50 that are made from a shape memory material and that intersect with each other. The tubular stent body 5 is configured to be adapted to anchor on the luminal wall of the aorta downstream of an aorta root in terms of an ejected flow of blood under systole pressure, and has an abluminal surface which confronts the luminal wall, and a luminal surface which is opposite to the abluminal surface, and which defines an interior space extending along a central axis in a lengthwise direction.

When expanded, the tubular stent body 5 further has distal and proximal end surfaces that are spaced apart from each other to define, in cooperation with the luminal surface, the interior space in the lengthwise direction.

The percutaneous intra-aortic ventricular assist device further includes a rigid suspension ring 52 that is held by the distal end surface of the tubular stent body 5 to surround the central axis, and a holding ring 53 that is held by the proximal end surface of the tubular stent body 5 to surround the central axis.

Figure 5:
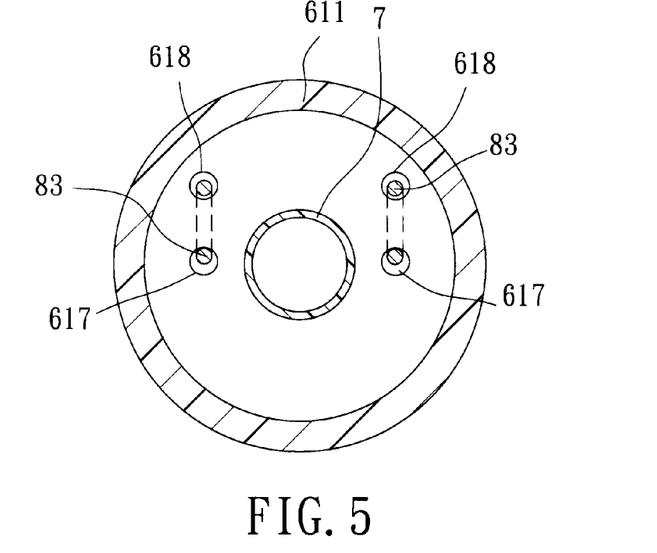
FIG. 5 is a cross-sectional view of a proximal tubular end of an inner tubular body to illustrate a first through-hole and a second through-hole of the inner tubular body according to the preferred embodiment.

The inner tubular body 6 is flexible, is detachably connected to the tubular stent body 5, and has an outer tubular surface which extends along the central axis to define, in cooperation with the luminal surface of the tubular stent body 5, a surrounding passage, and an inner tubular surface which is opposite to the outer tubular surface in radial directions, which defines an accommodation chamber, and which has a guiding slot unit that extends in the lengthwise direction to terminate at proximal and distal loci relative to the aorta root, and that extends radially through the outer tubular surface to communicate the surrounding passage with the accommodation chamber. In this embodiment, the inner tubular surface has four guiding slots 616 that constitute the guiding slot unit, and that are angularly disposed from one another about the central axis. The inner tubular body 6 further has an enlarged distal tubular end, and a proximal tubular end that is opposite to the enlarged distal tubular end in the lengthwise direction. The proximal tubular end is formed with an opening 613, two first through-holes 617 (shown in FIG. 5), and two second through-holes 618 (shown in FIG. 5). Preferably, the inner tubular body 6 includes a main portion 611 that has the guiding slots 616 and the proximal tubular end, and a shoulder portion 615 that has the enlarged distal tubular end.

The rigid suspension ring 52 of the tubular stent body 5 is configured of a dimension that permits the proximal tubular end of the inner tubular body 6 to pass through (i.e., the main portion 611 has a maximum external diameter smaller than a diameter of the rigid suspension ring 52) but retains the enlarged distal tubular end thereat. The holding ring 53 is configured of a dimension to engage the proximal tubular end. In this embodiment, the percutaneous intra-aortic ventricular assist device further includes a fastening member 612 disposed on the proximal tubular end of the inner tubular body 6 in order to permit the holding ring 53 to be in a threaded engagement with the proximal tubular end.

Preferably, the percutaneous intra-aortic ventricular assist device further includes a flexible guiding tubular body 9, a flexible duct 7, and a plurality of flexible partition members 92. The shoulder portion 615 of the inner tubular body 6 interconnects the guiding tubular body 9 and the main portion 611 of the inner tubular body 6. The guiding tubular body 9 has an outer wall having a diameter larger than the maximum external diameter of the main portion 611 of the inner tubular body 6, and an inner wall defining an internal space. When the percutaneous intra-aortic ventricular assist device is implanted in the aorta, the guiding tubular body 9 extends along the aorta and is led out of a patient's body (shown in FIGS. 7 and 8). The duct 7 is adapted for insertion of a catheter guide wire (not shown), extends along the accommodation chamber of the inner tubular body 6 and the internal space of the guiding tubular body 9, and has a proximal opening that is concentric with the opening 613 of the proximal tubular end of the inner tubular body 6. The partition members 92 are angularly spaced apart from each other in the internal space of the guiding tubular body 9, are respectively disposed between the inner wall of the guiding tubular body 9 and an exterior surface of the duct 7 so as to cooperatively define a plurality of compartments 90, and extend along the internal space of the guiding tubular body 9.

The vane member 87 is flexible, is disposed to be movable in the surrounding passage between proximal and distal limits that respectively correspond to the proximal and distal loci of the guiding slot unit, and that are apart from each other by a predetermined traveling length, and is configured to help force the ejected flow of the blood downstream when the vane member 87 is moved from the proximal limit towards the distal limit. In this embodiment, the vane member 87 is configured to surround the outer tubular surface of the inner tubular body 6.

Figure 6:
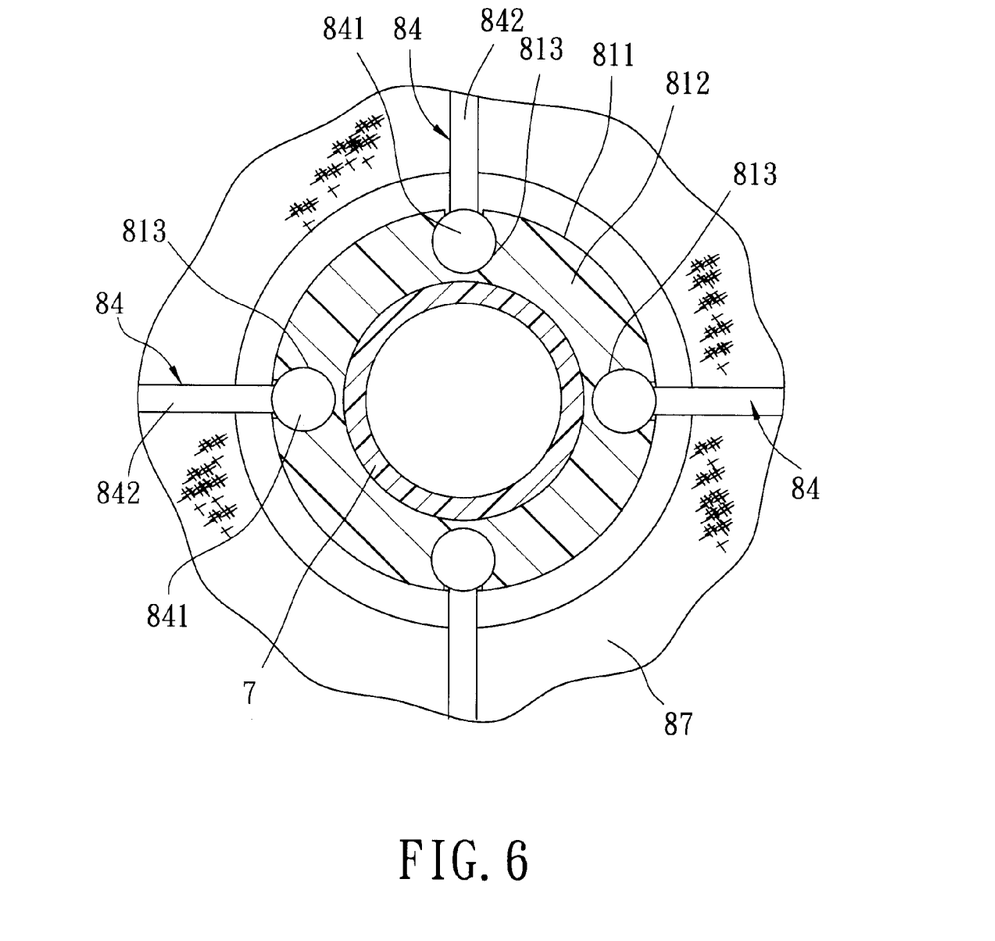
FIG. 6 is a partly cross-sectional view illustrating how ribs are respectively pivoted to anchoring regions of a carrier member according to the preferred embodiment.

The carrier member 81 is disposed to be movable in the accommodation chamber between the proximal and distal loci of the guiding slot unit. In this embodiment, the carrier member 81 is configured to be a tubular hub having a tubular bottom surface 812 and a tubular top surface 811 that is opposite to the tubular bottom surface 812 lengthwise, and is sleeved on the duct 7. The tubular bottom surface 812 has four cavities 813 that extend respectively in the lengthwise direction, that are angularly spaced apart from each other, and that respectively have a circular cross-section (shown in FIG. 6).

The tubular top surface 811 has an external diameter smaller than a maximum external diameter of the tubular bottom surface 812.

The rib unit is disposed to move along the guiding slot unit, and is configured to interconnect the carrier member 81 and the vane member 87 so as to permit the vane member 87 to be moved with the carrier member 81. In this embodiment, the rib unit includes four ribs 84 that are made from a shape memory metal, that are respectively disposed to move along the guiding slots 616, and that extend radially to respectively interconnect the vane member 87 and the carrier member 81. Each of the ribs 84 has an anchoring end 841 which is pivoted to the carrier member 81 at a respective one of anchored regions such that the vane member 87 is transformable from a folded position to a spread position so as to permit the vane member 87 to be unfolded into a spread form once the tubular stent body 5 is expanded at the site of implantation, and a protruding part 842 which extends through a respective one of the guiding slots 616 in order to interconnect the vane member 87 and the carrier member 81, and which has a terminal end 843 opposite to the anchoring end 841. Preferably, the anchoring end 841 of each of the ribs 84 is configured to be a spherical enlarged head (shown in FIG. 6). The cavities 813 of the carrier member 81 are able to respectively permit detachable insertion of the ribs 84 so as to locate each of the enlarged heads at the respective one of the anchored regions. When the vane member 87 is in the spread position, the distance between the two terminal ends 843 of the two opposite protruding parts 842 relative to the carrier member 81 is smaller than a diameter of the luminal surface of the tubular stent body 5.

The percutaneous intra-aortic ventricular assist device further includes a retaining ring 85 that is configured to detachably hoop the tubular bottom surface 812 of the tubular hub and to be disposed beneath the ribs 84 for guarding each of the enlarged heads against moving away from the respective one of the anchored regions, and that is configured to block each of the ribs 84 from being pivoted downwardly relative to the carrier member 81 when the protruding part 842 of each of the ribs 84 is disposed to contact the retaining ring 85. It should be noted that the carrier member 81 might include a limiting member to replace the retaining ring 85 and to block each of the ribs 84 from being pivoted downwardly relative to the carrier member 81 in other embodiments.

Referring to FIGS. 2, 3, 7, and 8, each of the first pulled strings 82 has first inner and outer ends which are opposite to each other lengthwise, and which are respectively connected to the tubular top surface 811 of the carrier member 81 and led out of the patient's body such that when the first outer end is pulled externally, the carrier member 81 is moved towards the distal locus of the guiding slot unit. From a respective one of the first inner ends, each of the first pulled strings 82 sequentially extends upwardly along the accommodation chamber of the inner tubular body 6 and a respective one of the compartments 90 in the guiding tubular body 9, and is led out of the patient's body.

Each of the second pulled strings 83 has a pair of second inner ends which are connected to the tubular bottom surface 812 of the carrier member 81, and a second outer end which is opposite to the pair of the second inner ends length wise, and which is led out of the patient's body such that when the second outer end is pulled externally, the carrier member 81 is moved towards the proximal locus of the guiding slot unit. Referring to FIGS. 3, 4, 5, 7, and 8, from a respective pair of the second inner ends, each of the second pulled strings 83 extends downwardly through a respective one of the first through-holes 617 and upwardly through a respective one of the second through-holes 618 in sequence. Afterwards, each of the second pulled strings 83 extends along the accommodation chamber of the inner tubular body 6 and a respective one of the compartments 90 in the guiding tubular body 9 in order, and is led out of the patient's body.

Referring to FIGS. 2, 3, 7, and 8, the percutaneous intra-aortic ventricular assist device further includes two third pulled strings 86. Each of the third pulled strings 86 has third inner and outer ends that are opposite to each other lengthwise, and that are respectively connected to the retaining ring 85 and led out of the patient's body. From a respective one of the third inner ends, each of the third pulled strings 86 successively extends upwardly along the accommodation chamber of the inner tubular body 6 and a respective one of the compartments 90 in the guiding tubular body 9, and is led out of the patient's body.

Referring to FIGS. 1, 7, and 8, in this embodiment, each of the first pulled strings 82 has an exposed segment that is disposed outside the patient's body and that has the first outer end. Two exposed segments of the first pulled strings 82 are entwined with each other for the sake of convenience. Similarly, each of the second pulled strings 83 has an exposed segment that is disposed outside the patient's body and that has the second outer end. Two exposed segments of the second pulled strings 83 are entwined with each other. Each of the third pulled strings 86 has an exposed segment that is disposed outside the patient's body and that has the third outer end. Two exposed segments of the third pulled strings 86 are entwined with each other.

Referring to FIGS. 2, 7, and 8, the alternately pulling mechanism 4 is placed outside the patient's body, and is disposed to couple with the first outer ends and the second outer ends respectively such that when the alternately pulling mechanism 4 is actuated to alternately pull the first outer ends and the second outer ends in a pulling direction respectively to displace the carrier member 81 to the distal and proximal loci of the guiding slot unit respectively, the second pulled strings 83 and the first pulled strings 82 are enabled respectively by alternately pulling of the first outer ends and the second outer ends to respectively permit the second outer ends and the first outer ends to tensely retrieve, concomitant with the alternate pulling of the first outer ends and the second outer ends respectively, the predetermined traveling length in a releasing direction that is opposite to the pulling direction. The third outer ends are coupled to the alternately pulling mechanism 4, such that the third outer ends are kept to move in synchronization with the first outer ends in both of the pulling and releasing directions so as to ensure each of the enlarged heads of the ribs 84 being guarded against moving away from the respective one of the anchored regions during both the systole and diastole actions.

In this embodiment, the alternately pulling mechanism 4 includes a base support 42, and a wheel member 41 that is rotatably mounted on the base support 42 about a rotating axis, and that includes a rim defining a circumferential guiding route to surround the rotating axis. The circumferential guiding route has first and second connected sites 411, 412 which are diametrically opposite to each other, and which are coupled with the first outer ends and the second outer ends respectively such that when one of pairs of the first pulled strings 82 and the second pulled strings 83 are pulled to be wound around the circumferential guiding route by virtue of rotating the wheel member 41 clockwise or counterclockwise, the other one of pairs of the first pulled strings 82 and the second pulled strings 83 are detached from the circumferential guiding route by the predetermined traveling length. Preferably, the first connected site 411 is also coupled with the third outer ends of the third pulled strings 86 such that the third outer ends are kept to move in synchronization with the first outer ends in both of the pulling and releasing directions.

It should be noted that a method of connecting the first, second, and third pulled strings 82, 83, 86 to the alternately pulling mechanism 4 is not limited to the abovementioned method.

The synchronizing member 3 is disposed to couple with the alternately pulling mechanism 4 so as to bring the pulling of the first outer ends and the second outer ends in the pulling direction in synchronization with the alternate systole and diastole actions. Preferably, the synchronizing member 3 includes a servomotor 31 that is disposed to alternately drive the wheel member 41 to rotate clockwise and counterclockwise, and that is adjustable to bring the pulling of the first outer ends and the second outer ends in the pulling direction in synchronization with the alternate systole and diastole actions.

The method of implanting the percutaneous intra-aortic ventricular assist device in the aorta is described as follows. Before implanting the percutaneous intra-aortic ventricular assist device in the aorta, the carrier member 81, the ribs 84, and the retaining ring 85 are required to be assembled together and to be subsequently disposed in the inner tubular body 6 outside the patient's body. Referring to FIGS. 1, 2, 3, and 4, each of the ribs 84 is inserted into a respective one of the cavities 813 such that the enlarged head of each of the ribs 84 is located at the respective one of the anchored regions. The retaining ring 85 is then moved upwardly relative to the tubular bottom surface 812 of the carrier member 81 to hoop the tubular bottom surface 812 and to be disposed beneath the ribs 84. Therefore, each of the ribs 84 is not pivotable downwardly relative to the carrier member 81 when the protruding part 842 is disposed to contact the retaining ring 85. In this embodiment, each of the ribs 84 is unable to be pivoted onto a horizontal plane that is transverse to the anchored regions. When the protruding part 842 of each of the ribs 84 is in contact with the retaining ring 85, each of the ribs 84 extends upwardly and obliquely from the respective one of the anchored regions such that each of the ribs 84 and the horizontal plane cooperatively define an angle that is greater than 0 degree.

Preferably, the main portion 611 of the inner tubular body 6 is composed of first and second segments (not shown) that are detachably connected. The first, second, and third pulled strings 82, 83, 86, and the carrier member 81 with the ribs 84 and the retaining ring 85 are disposed in the first segment. Afterwards, the second segment is connected to the first segment. Each of the ribs 84 is pivoted downwardly relative to the carrier member 81 in the main portion 611 so as to extend through a respective one of the guiding slots 616. The vane member 87 is subsequently connected to the protruding part 842 of each of the ribs 84. It should be noted that a method of disposing the first, second, and third pulled strings 82, 83, 86, and the carrier member 81 with the ribs 84 and the retaining ring 85 in the inner tubular body 6 is not restricted to the abovementioned method.

The tubular stent body 5 can be stretched in a direction along the central axis and contracted inwardly toward the central axis by virtue of a guide wire (not shown) and a pulling string (not shown). Referring to FIGS. 2, 7, and 8, thus, the tubular stent body 5 can be placed into a catheter (not shown) and percutaneously delivered to the ascending aorta 20 via cardiac catheterization. It should be noted that the tubular stent body 5 is able to be disposed in a descending aorta or other parts of the aorta in other embodiments. Since the feature of the invention does not reside in a method of delivering the tubular stent body 5 to the ascending aorta 20 via cardiac catheterization, further details of the same are omitted herein for the sake of brevity.

After the tubular stent body 5 is disposed in the ascending aorta 20, the guide wire is left in the aorta and is used as a guiding rail for the duct 7. Outside the patient's body, the duct 7 is inserted into the guiding tubular body 9 and the inner tubular body 6 in sequence. When the duct 7 is inserted into the inner tubular body 6, the duct 7 is passed through the carrier member 81 such that the carrier member 81 is sleeved on the duct 7. The inner tubular body 6 and the guiding tubular body 9 are sequentially inserted into the aorta when the duct 7 is sleeved on the guide wire and is moved along the guide wire with the inner tubular body 6 and the guiding tubular body 9. When the proximal tubular end of the inner tubular body 6 is passed through the rigid suspension ring 52 and is disposed in the holding ring 53, the inner tubular body 6 is rotated relative to the tubular stent body 5 such that the holding ring 53 is in a threaded engagement with the proximal tubular end. Consequently, the inner tubular body 6, the carrier member 81 with the ribs 84 pivoted thereto and with the retaining ring 85 hooped thereon, and the vane member 87 are installed in the ascending aorta 20. The guiding tubular body 9 connected to the inner tubular body 6 extends along the aorta and is led out of the patient's body. The guide wire is pulled out from the patient's body after the implantation of the percutaneous intra-aortic ventricular assist device.

When the percutaneous intra-aortic ventricular assist device is completely implanted in the aorta, the first, second, and third pulled strings 82, 83, 86 are led out of the patient's body and connected to the wheel member 41 of the alternately pulling mechanism 4. The first and third pulled strings 82, 86 are tensely stretched and connected to the first connected site 411 of the wheel member 41. The second pulled strings 83 are tensely stretched and connected to the second connected site 412 of the wheel member 41.

A computer program based on electrocardiac signals is applied to the synchronizing member 3 so as to rotate the wheel member 41 in synchronization with the alternate systole and diastole actions. Referring to FIGS. 2 and 8, when the left ventricle 21 pumps blood into the ascending aorta 20 during the systole, the wheel member 41 is rotated clockwise such that the first and third pulled strings 82, 86 are pulled to be wound around the circumferential guiding route, and such that the second pulled strings 83 are detached from the circumferential guiding route. Therefore, the carrier member 81 is moved from the proximal locus towards the distal locus so as to move the vane member 87 from the proximal limit towards the distal limit. At this time, due to a resistance force that is created by blood downstream of the vane member 87, the vane member 87 is transformed from a folded position, where each of the ribs 84 is disposed adjacent to a respective one of the guiding slots 616 (shown in FIG. 7), to a spread position, where the protruding part 842 of each of the ribs 84 is disposed to contact the retaining ring 85, and the protruding part 842 of each of the ribs 84 disposed adjacent to the respective one of the guiding slots 616 moves towards the retaining ring 85 that blocks each of the ribs 84 from being pivotable downwardly beneath the horizontal plane. The vane member 87 in the spread form is able to push the ejected flow of the blood downstream when the vane member 87 is moved towards the distal limit. A negative pressure is induced as well when the vane member 87 is moved towards the distal limit and is capable of providing a suction force to pump blood into the ascending aorta 20 from the left ventricle 21. Thus, the percutaneous intra-aortic ventricular assist device is able to efficiently assist the left ventricle 21 in pumping blood even during severe left-sided heart failure.

Referring to FIGS. 2 and 7, when the wheel member 41 is rotated counterclockwise during the diastole such that the second pulled strings 83 are pulled to be wound around the circumferential guiding route, and such that the first and third pulled strings 82, 86 are detached from the circumferential guiding route, the carrier member 81 is moved from the distal locus towards the proximal locus so as to move the vane member 87 from the distal limit towards the proximal limit. At this time, since a resistance force that is created by blood upstream of the vane member 87 pushes the vane member 87 and the protruding part 842 of each of the ribs 84, the vane member 87 in the spread position (shown in FIG. 8) is transformed to the folded position, and the protruding part 842 of each of the ribs 84 moves towards a respective one of the guiding slots 616 from the retaining ring 85. On account of the vane member 87 being in the folded position, the blood in the ascending aorta 20 cannot be blocked by the vane member 87 and is able to be transported to other organs and tissues of a human body.

Figure 9:
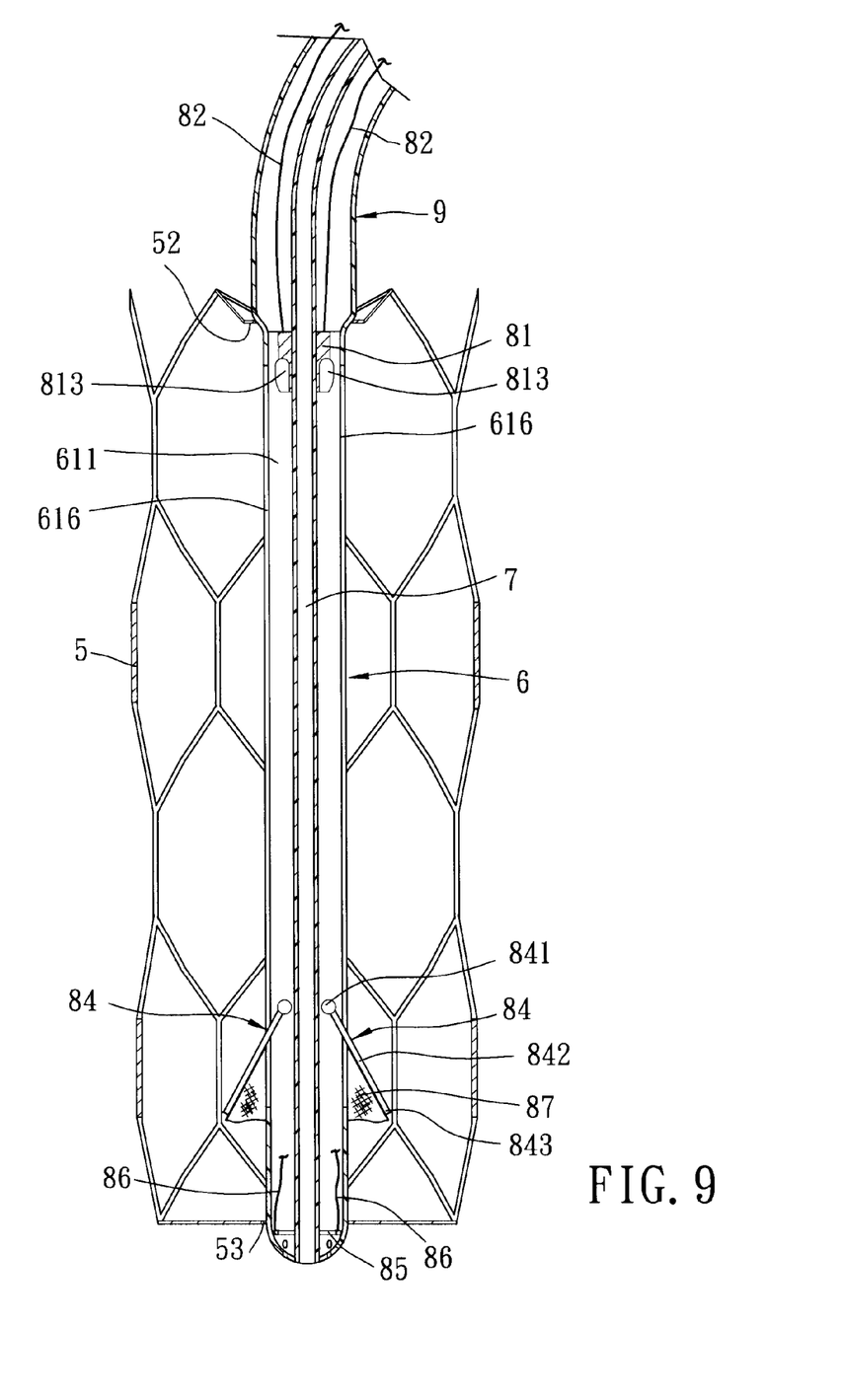
FIG. 9 is a fragmentary sectional view illustrating how a retaining ring is detached from the carrier member so as to permit the ribs to be detached from the carrier member according to the preferred embodiment.

The percutaneous intra-aortic ventricular assist device of this invention can be detached from the patient's body. Referring to FIGS. 2 and 9, the third pulled strings 86 are first disconnected from the wheel member 41 (shown in FIGS. 7 and 8) such that the third pulled strings 86 are incapable of immobilizing the retaining ring 85 on the carrier member 81. Subsequently, the first pulled strings 82 are pulled to be wound around the circumferential guiding route in order to move the carrier member 81 towards the distal locus. Since the retaining ring 85 is not immobilized on the tubular bottom surface 812 of the carrier member 81, the enlarged head of each of the ribs 84 moves away from the respective one of the anchored regions when the carrier member 81 is moved towards the distal locus. In the meantime, from the respective one of the cavities 813, the ribs 84 together with the vane member 87 drop towards the proximal tubular end of the inner tubular body 6 so as to force the retaining ring 85 to be detached from the tubular bottom surface 812. Consequently, the retaining ring 85 drops into the proximal tubular end. The vane member 87 and the ribs 84 drop towards the proximal tubular end until the ribs 84 reach the proximal locus of the guiding slot unit.

Finally, cardiac catheterization is conducted. The guide wire is extended through the duct 7. A catheter (not shown) is inserted into the patient's body and is sleeved on the guiding tubular body 9. The inner tubular body 6 is rotated relative to the tubular stent body 5 so as to disengage the proximal tubular end of the inner tubular body 6 from the holding ring 53. The inner tubular body 6 is pulled into the catheter from the tubular stent body 5 by virtue of the guide wire. The carrier member 81, the ribs 84, the vane member 87, and the retaining ring 85 are hence pulled into the catheter. The catheter is pulled out from the patient's body to complete detachment of the percutaneous intra-aortic ventricular assist device except for the tubular stent body 5. The tubular stent body 5 can be left in the patient's body for future implantation. The percutaneous intra-aortic ventricular assist device of this invention is suitable for short-term and long-term use.

While the present invention has been described in connection with what is considered the most practical and preferred embodiment, it is understood that this invention is not limited to the disclosed embodiment but is intended to cover various arrangements included within the spirit and scope of the broadest interpretation and equivalent arrangements.

What is claimed is:

1. A percutaneous intra-aortic ventricular assist device adapted for implantation in an aorta that has a luminal wall, said percutaneous intra-aortic ventricular assist device comprising:

a tubular stent body made from a material expandable at a site of implantation, configured to be adapted to anchor on the luminal wall of the aorta downstream of an aorta root in terms of an ejected flow of blood under systole pressure, and having an abluminal surface which confronts the luminal wall, and a luminal surface which is opposite to said abluminal surface, and which defines an interior space extending along a central axis in a lengthwise direction;

an inner tubular body connected to said tubular stent body and having an outer tubular surface which extends along the central axis to define, in cooperation with said luminal surface of said tubular stent body, a surrounding passage, and an inner tubular surface which is opposite to said outer tubular surface in radial directions, which defines an accommodation chamber, and which has a guiding slot unit that extends in the lengthwise direction to terminate at proximal and distal loci relative to the aorta root, and that extends radially through said outer tubular surface to communicate said surrounding passage with said accommodation chamber;

a vane member disposed to be movable in said surrounding passage between proximal and distal limits that respectively correspond to said proximal and distal loci of said guiding slot unit, and that are apart from each other by a predetermined traveling length, and configured to help force the ejected flow of the blood downstream when said vane member is moved from said proximal limit towards said distal limit;

a carrier member disposed to be movable in said accommodation chamber between said proximal and distal loci of said guiding slot unit;

a rib unit disposed to move along said guiding slot unit, and configured to interconnect said carrier member and said vane member so as to permit said vane member to be moved with said carrier member;

a first pulled string having first inner and outer ends which are opposite to each other lengthwise, and which are respectively connected to said carrier member and led out of a patient's body such that when said first outer end is pulled externally, said carrier member is moved towards said distal locus of said guiding slot unit;

a second pulled string having second inner and outer ends which are opposite to each other lengthwise, and which are respectively connected to said carrier member and led out of the patient's body such that when said second outer end is pulled externally, said carrier member is moved towards said proximal locus of said guiding slot unit;

an alternately pulling mechanism disposed to couple with said first and second outer ends respectively such that when said alternately pulling mechanism is actuated to alternately pull said first and second outer ends in a pulling direction respectively to displace said carrier member to said distal and proximal loci of said guiding slot unit respectively, said second and first pulled strings are enabled respectively by alternately pulling of said first and second outer ends to respectively permit said second and first outer ends to tensely retrieve, concomitant with the alternate pulling of said first and second outer ends respectively, the predetermined traveling length in a releasing direction that is opposite to the pulling direction; and a synchronizing member disposed to couple with said alternately pulling mechanism so as to bring the pulling of said first and second outer ends in the pulling direction in synchronization with the alternate systole and diastole actions.

2. The percutaneous intra-aortic ventricular assist device as claimed in claim 1, wherein:

said vane member is configured to surround said outer tubular surface of said inner tubular body;

said inner tubular surface of said inner tubular body has a plurality of guiding slots which constitute said guiding slot unit, and which are angularly disposed from one another about the central axis; and said rib unit includes a plurality of ribs which are respectively disposed to move along said guiding slots, and which extend radially to respectively interconnect said vane member and said carrier member, each of said ribs having an anchoring end which is pivoted to said carrier member at a respective one of anchored regions such that said vane member is transformable from a folded position to a spread position so as to permit said vane member to be unfolded into a spread form once said tubular stent body is expanded at the site of implantation.

3. The percutaneous intra-aortic ventricular assist device as claimed in claim 2, wherein said anchoring end is configured to be an enlarged head, said carrier member being configured to be a tubular hub which has a tubular bottom surface that has a plurality of cavities extending respectively in the lengthwise direction to permit insertion of said ribs respectively so as to locate each of said enlarged heads at the respective one of said anchored regions, said percutaneous intra-aortic ventricular assist device further comprising a retaining ring which is configured to hoop said tubular hub and to be disposed beneath said ribs for guarding each of said enlarged heads against moving away from the respective one of said anchored regions.

4. The percutaneous intra-aortic ventricular assist device as claimed in claim 3, further comprising a third pulled string having third inner and outer ends which are opposite to each other lengthwise, and which are respectively connected to said retaining ring and led out of the patient's body, said third outer end being coupled to said alternately pulling mechanism, such that said third outer end is kept to move in synchronization with said first outer end in both of the pulling and releasing directions so as to ensure each of said enlarged heads being guarded against moving away from the respective one of said anchored regions during both the systole and diastole actions.

5. The percutaneous intra-aortic ventricular assist device as claimed in claim 1, wherein said inner tubular body further has an enlarged distal tubular end, and a proximal tubular end which is opposite to said enlarged distal tubular end in the lengthwise direction, said expanded tubular stent body further having distal and proximal end surfaces that are spaced apart from each other to define, in cooperation with said luminal surface, said interior space in the lengthwise direction, said percutaneous intra-aortic ventricular assist device further comprising a rigid suspension ring which is held by said distal end surface to surround the central axis, and which is configured of a dimension that permits said proximal tubular end to pass through, but retains said enlarged distal tubular end thereat, and a holding ring which is held by said proximal end surface to surround the central axis, and which is configured of a dimension to engage said proximal tubular end therein.

6. The percutaneous intra-aortic ventricular assist device as claimed in claim 5, further comprising a fastening member disposed to permit said holding ring to be in a threaded engagement with said proximal tubular end of said inner tubular body.

7. The percutaneous intra-aortic ventricular assist device as claimed in claim 6, wherein said alternately pulling mechanism includes a base support, and a wheel member which is rotatably mounted on said base support about a rotating axis, and which includes a rim that defines a circumferential guiding route to surround the rotating axis, said circumferential guiding route having first and second connected sites which are diametrically opposite to each other, and which are coupled with said first and second outer ends respectively such that when one of said first and second pulled strings is pulled to be wound around said circumferential guiding route for the predetermined traveling length by virtue of rotating said wheel member clockwise or counterclockwise, the other one of said first and second pulled strings is detached from said circumferential guiding route by the predetermined traveling length, said synchronizing member including a servomotor which is disposed to alternately drive said wheel member to rotate clockwise and counterclockwise, and which is adjustable to bring the pulling of said first and second outer ends in the pulling direction in synchronization with the alternate systole and diastole actions.

* * * * *